(12) United States Patent
Doherty et al.

(10) Patent No.: US 10,820,798 B2
(45) Date of Patent: Nov. 3, 2020

(54) NON-COHERENT LIGHT DELIVERY SYSTEM AND METHOD

(71) Applicant: Eidolon Optical, LLC, Natick, MA (US)

(72) Inventors: Victor J. Doherty, Wellesley, MA (US); Dina Aouani, Cambridge, MA (US); Michael S. Costello, Newton, MA (US); Sormeh Yazdi, Cambridge, MA (US)

(73) Assignee: EIDOLON OPTICAL, LLC, Natick, MA (US)

( * ) Notice: Subject to any disclaimer, the term of this patent is extended or adjusted under 35 U.S.C. 154(b) by 155 days.

(21) Appl. No.: 16/053,915

(22) Filed: Aug. 3, 2018

(65) Prior Publication Data

US 2019/0038131 A1 Feb. 7, 2019

Related U.S. Application Data

(60) Provisional application No. 62/541,578, filed on Aug. 4, 2017.

(51) Int. Cl.
*A61B 3/135* (2006.01)
*A61F 9/008* (2006.01)

(52) U.S. Cl.
CPC .......... *A61B 3/135* (2013.01); *A61F 9/00821* (2013.01); *A61F 2009/00863* (2013.01); *A61F 2009/00872* (2013.01)

(58) Field of Classification Search
CPC ................. A61B 3/135; A61F 9/00821; A61F 2009/00872; A61F 2009/00863
USPC ........................................ 351/200, 205, 214
See application file for complete search history.

(56) References Cited

U.S. PATENT DOCUMENTS

2004/0254619 A1  12/2004  Feuermann et al.
2016/0291234 A1*  10/2016  Qiu ...................... G02B 6/0011

OTHER PUBLICATIONS

Gordon, J.M., Feuermann, D., Huleihil, M., Mizrahi, S., and Shaco-Levy, R. (2003). Solar surgery. Journal of Applied Physics, 93(8), 4843-4851.

* cited by examiner

*Primary Examiner* — Tuyen Tra
(74) *Attorney, Agent, or Firm* — Carlson, Gaskey & Olds, P.C.

(57) ABSTRACT

A light delivery system according to an example of the present disclosure includes a solar tracker that has a rectangular aperture that delivers light to a quadrant detector, a light collector configured to capture light from an incoherent light source, the captured light being sunlight, a delivery optics unit for delivering the captured light to a target object, and an optical fiber unit optically connects an output of the light collector to the delivery optics unit. A method of performing a surgical procedure, including an iridectomy procedure, is also disclosed.

19 Claims, 11 Drawing Sheets

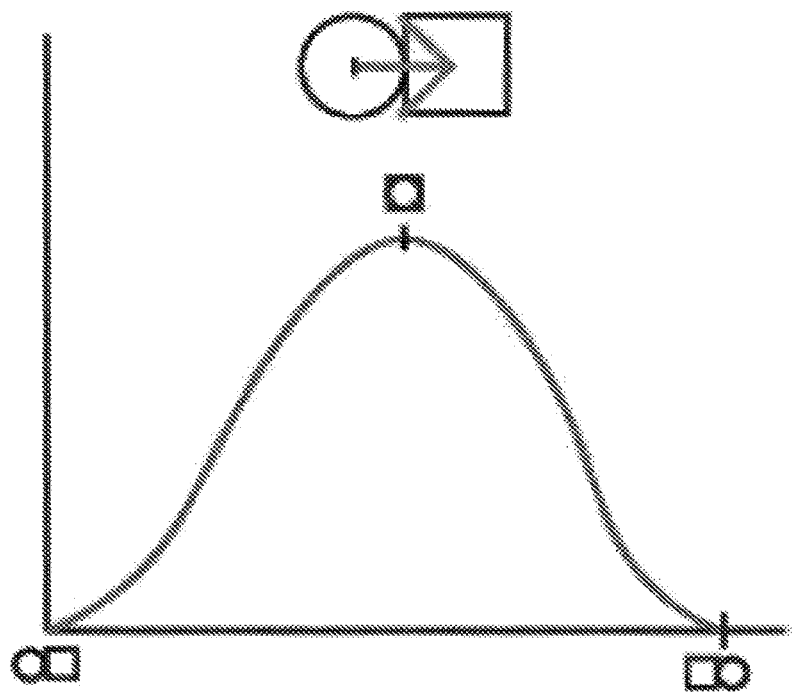
FIG. 9
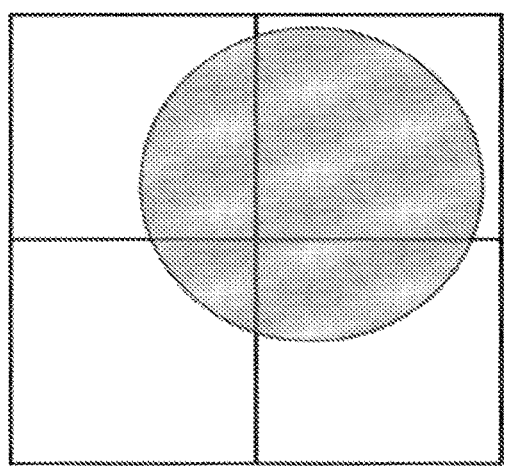 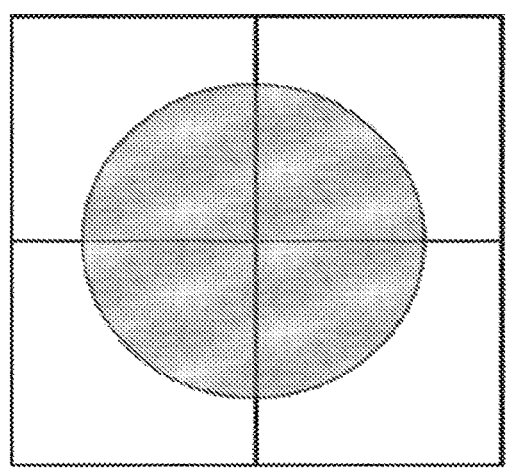
FIG. 10A　　　　　　　　　FIG. 10B

X=0, S=0

X=1, S=0.61

X=2, S=π/2

X=3, S=2.53

X=4, S=π

X=0, S=0

X=1, S=1

X=2, S=2

X=3, S=3

X=4, S=4

NON-COHERENT LIGHT DELIVERY SYSTEM AND METHOD

CROSS-REFERENCE TO RELATED APPLICATIONS

The present disclosure claims priority to U.S. Provisional Patent Application No. 62/541,578, filed on Aug. 4, 2017, herein incorporated by reference in its entirety.

BACKGROUND

Each year, hundreds of thousands of people in rural China go blind as a result of angle-closure glaucoma. Angle-closure glaucoma prevents the aqueous humor to circulate freely within the eyeball, which leads to higher intraocular pressure. This can result in optic nerve damage and loss of vision if not properly treated in a timely manner.

In the United States and Europe, ophthalmologists treat the condition by perforating the iris of the patient to release the intraocular pressure with a laser. That procedure is called a laser iridectomy (also known as iridotomy). However, of the approximately 20,000 ophthalmic clinics in China, almost none can afford the safer laser iridectomy system. Hence, there is the potential for a high demand for lower-cost iridectomy systems that is as precise as an iridotomy system.

SUMMARY

A light delivery system according to an example of the present disclosure includes a solar tracker that has a rectangular aperture that delivers light to a quadrant detector, a light collector configured to capture light from an incoherent light source, the captured light being sunlight, a delivery optics unit for delivering the captured light to a target object, and an optical fiber unit optically connect an output of the light collector to the delivery optics unit.

In a further embodiment of any of the foregoing embodiments, the delivery optics unit includes a corneal microscope or an ophthalmoscope.

In a further embodiment of any of the foregoing embodiments, the delivery optics unit includes a slit lamp.

In a further embodiment of any of the foregoing embodiments, the delivery optics unit includes a zoom lens.

In a further embodiment of any of the foregoing embodiments, the solar tracker is configured to output a control signal, and further includes a multi-axis mount communicatively coupled to the solar tracker and configured to change, in response to the control signal, at least one of an elevation angle and azimuthal angle of the light collector.

In a further embodiment of any of the foregoing embodiments, the solar tracker includes a lens between the rectangular aperture and the quadrant detector.

In a further embodiment of any of the foregoing embodiments, the lens forms a rectangular image on the quadrant detector in response to receiving light from the rectangular aperture.

In a further embodiment of any of the foregoing embodiments, the rectangular aperture corresponds to one of a plurality of progressively sized square apertures defined by a sliding bar.

In a further embodiment of any of the foregoing embodiments, the light collector includes an aspheric lens and an aplanat configured to focus the captured light to an image at an image plane that is coplanar with an end of the optical fiber unit.

In a further embodiment of any of the foregoing embodiments, the light collector defines a collection area exceeding one hundred square centimeters.

A method of performing a surgical procedure according to an example of the present disclosure includes determining a position of an incoherent light source, that has delivering light from the incoherent light source through a square or rectangular aperture to form a rectangular image on a quadrant detector, capturing light from the incoherent light source in response to determining the position, communicating the captured light to an optical fiber, and forming an hole at a location on a target object by directing the captured light from the optical fiber onto the location.

In a further embodiment of any of the foregoing embodiments, the light is sunlight.

In a further embodiment of any of the foregoing embodiments, the method includes prior to the step of forming the hole, communicating the captured light from the optical fiber to a delivery optics unit.

In a further embodiment of any of the foregoing embodiments, the delivery optics unit includes a corneal microscope.

In a further embodiment of any of the foregoing embodiments, the delivery optics unit includes a slit lamp.

In a further embodiment of any of the foregoing embodiments, an optical power of the captured light communicated to the optical fiber is greater than 1 Watt.

In a further embodiment of any of the foregoing embodiments, the forming step results in the hole having a diameter of less than six-hundred micrometers.

In a further embodiment of any of the foregoing embodiments, the forming step results in the hole having a diameter of less than seventy micrometers.

In a further embodiment of any of the foregoing embodiments, the target object is soft tissue.

In a further embodiment of any of the foregoing embodiments, the soft tissue is tissue of an eye.

BRIEF DESCRIPTION OF THE DRAWINGS

FIG. 9 is a graphical depiction of the convolution of circle and a square, which represents the non-linear response of a conventional quad-cell tracking system.

FIG. 10A illustrates misalignment of the incident light intensity and quad cell of FIG. 9.

FIG. 10B illustrates perfect alignment of the incident light intensity and quad cell of FIG. 9.

DETAILED DESCRIPTION

The present disclosure presents an apparatus to track and collect light energy, from a non-coherent light source to provide an alternative to fiber optic lasers as well as lasers with fiber optic delivery systems in applications that heat up, burn, shape, cut, dehydrate or energize any given material. In particular, the present disclosure relates to tracking and collecting sunlight to perform a surgical procedure that burns cell tissues. More specifically the invention describes a new apparatus to perform eye surgery to cure angle-closure glaucoma, such as an iridectomy.

An incoherent-light iridectomy system includes a light collector, delivery optics, and an optical fiber unit. The light collector is configured to capture light. The delivery optics unit is configured to deliver the captured light to an eye. The optical fiber unit optically connects an output of the light collector to the delivery optics unit. An incoherent-light iridectomy method includes forming a hole at a location on an eye by directing light output from an optical fiber onto the location.

An iridotomy is an ophthalmic surgical operation that uses a laser to make an incision into a patient's iris (or iridectomy), underneath the upper eyelid. These perforations of the eye tissue allow the aqueous humor to circulate freely into the eye. Therefore, the pressure inside the eye can come to equilibrium with the pressure exerted at the front of the eye between the iris and the cornea, which eliminates the abnormal pressure in the eye caused by glaucoma and thus prevent damages to the retina and ultimately blindness.

Figure 1:
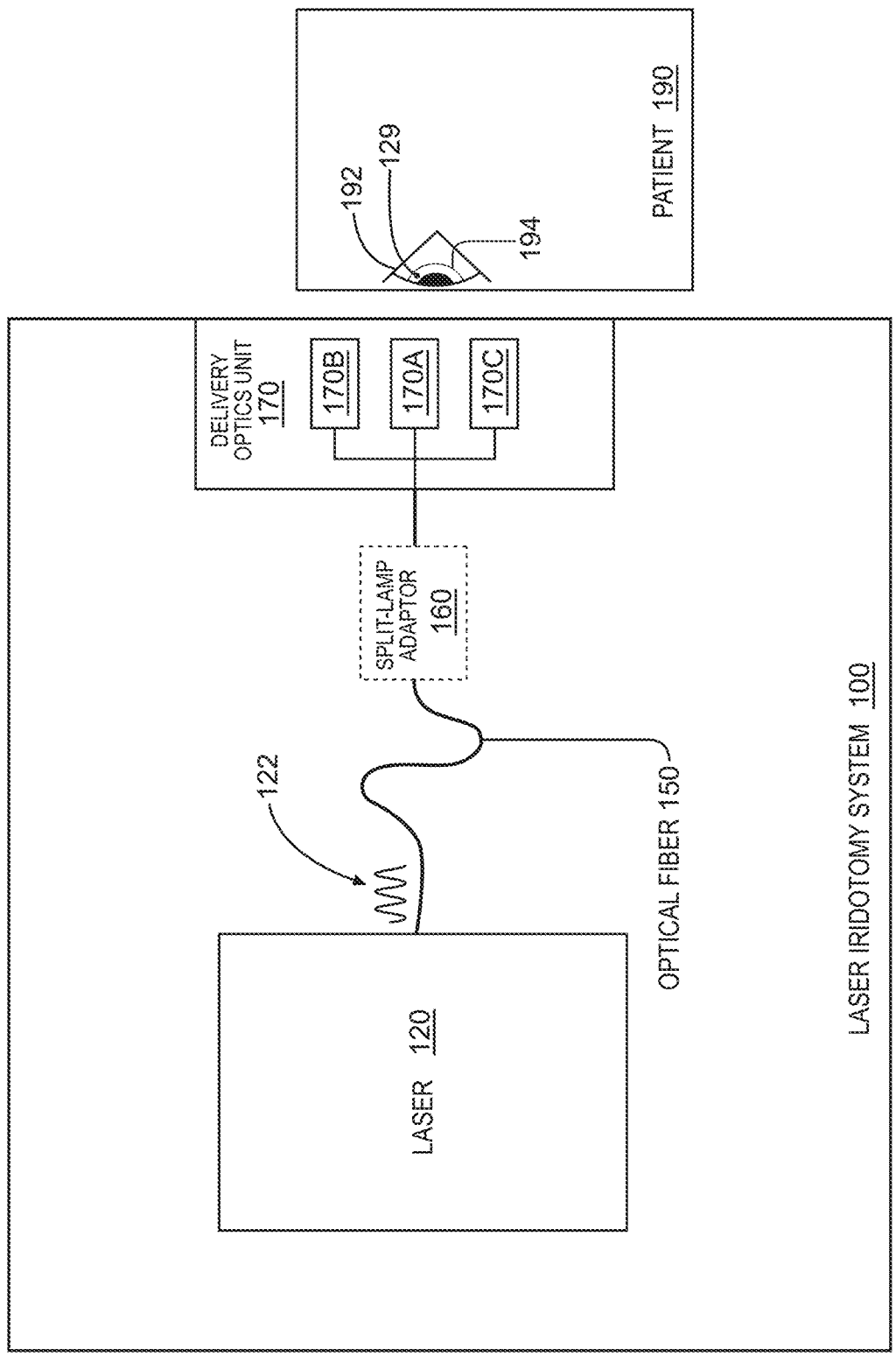
FIG. 1 is a schematic diagram of a typical laser iridectomy system.

FIG. 1 is a schematic diagram of a light delivery system 100 and a patient 190. Patient 190 has an eye 192 with an iris 194. In the illustrated example of FIG. 1, the light delivery system 100 is a yttrium aluminum garnet (YAG)-laser iridectomy system 100 that includes a laser 120 coupled to an optical fiber 150, which is coupled to a delivery optics unit 170. Laser 120 produces light 122 that propagates through optical fiber 150 to iris 194 via delivery optics unit 170. Laser 120 is a frequency-doubled Nd:YAG (neodymium-doped yttrium aluminum garnet) laser operating at $\lambda_0$=532 nm. Delivery optics unit 170 is for example a diagnostic slit lamp instrument (a.k.a. a slit-lamp microscope) used in the art that includes a slit lamp 170A, a corneal microscope 170B and an ophthalmoscope 170C. Delivery optics unit 170 can include a fixed focal lens or can include a zoom lens that can more closely matches the required focal lens. When delivery optics unit 170 is a diagnostic slit lamp, laser iridectomy system 100 may also include a slit-lamp adaptor 160 for forming light 122 into an appropriately-sized spot 129 on a localized region or location of a target object, such as iris 194.

In an embodiment of an iridectomy system disclosed herein, a fiber-coupled incoherent light source replaces laser 120, resulting in an incoherent-light iridectomy system that is in a viable price range of the aforementioned ophthalmic clinics. In one embodiment, an incoherent-light iridectomy system includes a light collector, a delivery optics unit, and an optical fiber unit. The light collector is configured to capture light. The delivery optics unit is configured to deliver the captured light to an eye. The optical fiber unit optically connects an output of the light collector to the delivery optics unit. In another embodiment, an incoherent-light iridectomy method includes forming a hole at a location on an eye by directing light output from an optical fiber onto the location.

Figure 2:
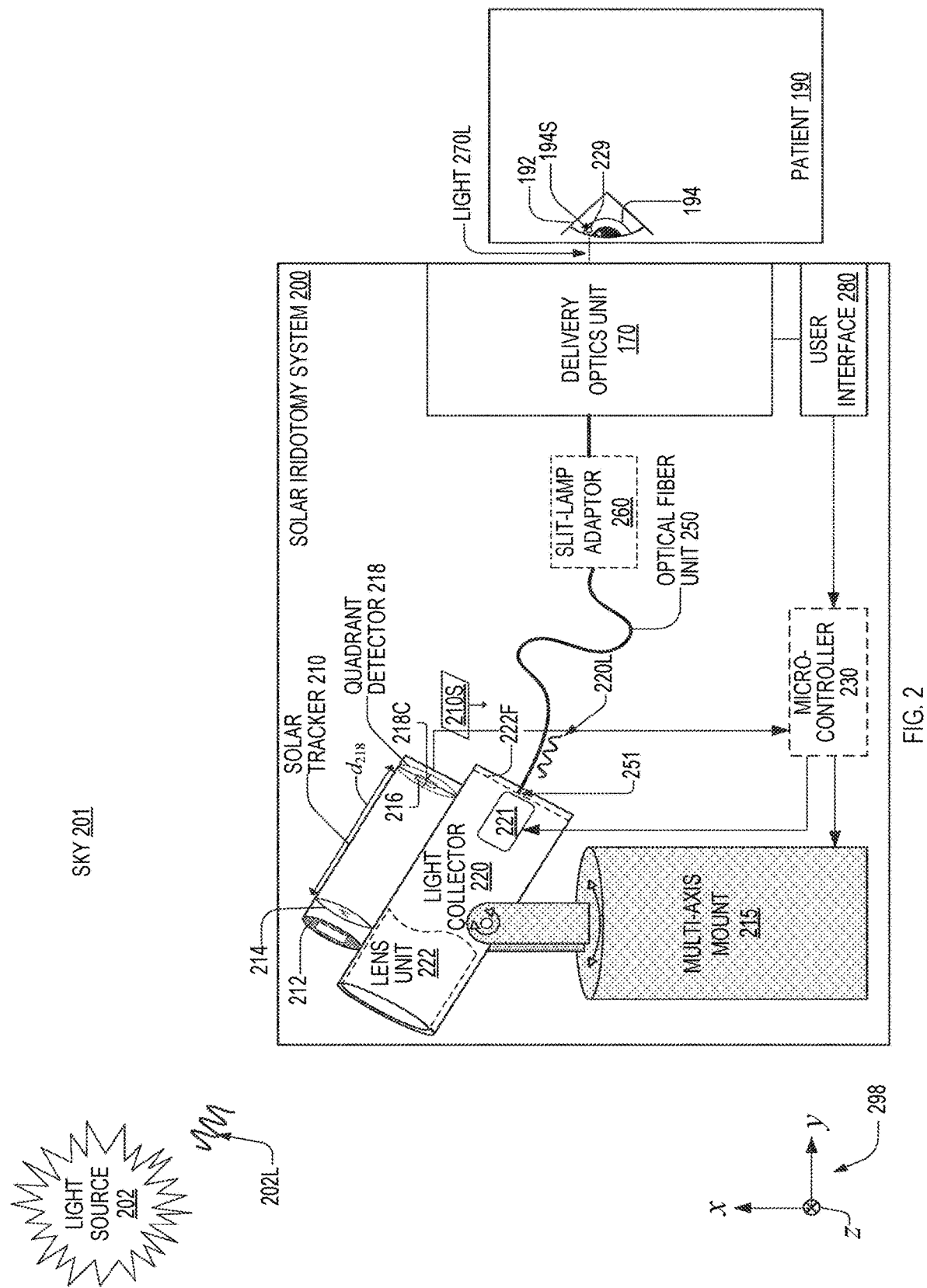
FIG. 2 is a schematic diagram of an incoherent-light iridectomy system, in an embodiment.

FIG. 2 is a schematic diagram of a light delivery system 200 and patient 190 beneath a light source 202 in sky 201. In the illustrated example of FIG. 2, the light delivery system 200 is an incoherent-light iridectomy system 200 that includes an optical fiber unit 250, and delivery optics unit 170. The light delivery system 200 can capture sunlight or other incoherent light from a light source 202. For example, light source 202 may be the Sun, as illustrated in FIG. 2, in which case incoherent-light iridectomy system 200, in some embodiments, also includes a solar tracker 210, a light collector 220, and a multi-axis mount 215.

While system 200 is referred to herein as an "incoherent-light iridectomy system," system 200 may be employed in applications other than iridectomies without departing from the scope hereof. Such applications include other medical procedures. In ophthalmology, it can be used to perform trabeculotomy, trabeculoplasty other retinal procedures (e.g., photocoagulation), cataract surgery, posterior capsulotomy, radial keratotomy, keratomileusis, intrastromal ablation, sclerotomies (both internal and external), to fragment of the interior of the lens and to treat a lack of homogeneity in the vitreous body.

System 200 may also be employed in applications other than iridectomies without departing from the scope hereof such as dermatological procedures. Those include, but are not limited to the removal of pigmented lesions, sun-damaged skin, tissue vaporization, warts, and tattoos. System 200 may also be employed in applications other than iridectomies without departing from the scope hereof such as dental and endodontic procedures (e.g. plaque removal, sterilization, filing material removal, dentures and dental bridges welding.) System 200 may also be employed in applications other than iridectomies without departing from the scope hereof such as gynecologic procedures (e.g. vulvar intraepithelial neoplasia (VIN), vaginal intraepithelial neoplasia (VAIN), cervical intraepithelial neoplasia (CIN), endometriosis, obstruction of the uterine tube, sterilization, twin-twin transfusion syndrome). System 200 may also be employed in applications other than iridectomies without departing from the scope hereof such as common urological procedures (e.g. photo-coagulation, photodynamic therapy, transurethral ultrasound-guided laser-induced prostatectomy (TULIP) and laser-induced interstitial thermotherapy (LITT)).

System 200 may also be employed in applications other than iridectomies without departing from the scope hereof such as angioplasty and cardiological procedures (e.g. laser angioplasty). System 200 may also be employed in applications other than iridectomies without departing from the scope hereof such as orthopedic procedures (e.g. osteotomies, laser meniscectomy). System 200 may also be employed in applications other than iridectomies without departing from the scope hereof such as gastroenterological procedures (e.g. photocoagulation, vaporization for recanalization of stenoses, widening of stenoses, tumor removal). System 200 may also be employed in applications other than iridectomies without departing from the scope hereof such as gastroenterological procedures (e.g. Blood vessel coagulation, stapedectomy and stapedotomy.

Other medical applications include but are not limited to wound cauterization, tumor treatment and removal. This light delivery apparatus also covers industrial applications of system 200 such as heating, engraving, marking, cutting, burning, welding, and weaponry.

During operation, delivery optics unit 170 delivers an amount of light or energy to a localized region of an object, such as tissue or other organic material, and/or inorganic material. The delivery optics unit 170 can deliver the amount of light or energy to the localized region to alter a characteristic of the targeted region, such as incisions or removal of tissue or other material.

Alternatively, light source 202 may be a terrestrial incoherent light source such as a broadband halogen fiber optic illuminator or a solid-state plasma light source that emits, for example, at least four watts of visible light. Herein, incoherent light refers to electromagnetic radiation that is at least one of temporally and spatially incoherent. In an embodiment, incoherent-light iridectomy system 200 includes light source 202, which is optically coupled to light collector 220, and does not include solar tracker 210 or multi-axis mount 215.

Light collector 220 collects light 202L from light source 202 and outputs light 220L that propagates through optical fiber unit 250 to iris 194 via delivery optics unit 170. Incoherent-light iridectomy system 200 may also include a slit-lamp adaptor 260 for forming the output of optical fiber unit 250 into an appropriately-sized spot 229 on iris 194. Spot 229 for example has a diameter between two hundred micrometers and six hundred micrometers. Spot 229 may have a diameter outside of this range, between fifty and seventy micrometers for example, without departing from the scope hereof.

Solar tracker 210 and light collector 220 may be oriented at a same elevation angle and a same azimuthal angle with respect to a coordinate system 298. The elevation angle is about a line parallel to the z-axis. The azimuthal angle is about a line parallel to the x-axis.

Solar tracker 210 detects light 202L and outputs a control signal 210S. Control signal 210S controls multi-axis mount 215 such that multi-axis mount 215 changes orientations of solar tracker 210 maximize the amount of light 202L collected by solar tracker 210, and hence also by light collector 220, as light source 202 traverses sky 201.

Solar tracker 210 includes a lens 214 and a quadrant detector 218. Lens 214 is for example a doublet. Quadrant detector 218 has a detector center 218C, wherein an optical axis of lens 214 intersects detector center 218C. Solar tracker 210 may also include an aperture 212 aligned with lens 214 and quadrant detector 218. Aperture 212 does not change coherence properties of light propagating therethrough. Aperture 212 is for example rectangular (e.g., a square) such that lens 214 produces an image 216 of light source 202 on quadrant detector 218 that, neglecting diffraction, has the same shape as aperture 212. When aperture 212 is rectangular, the response of each quadrant of quadrant detector 218 is a linear function of a distance between detector center 218C and a center of image 216, such that control signal 210S is similarly linear. Such a linear response of quadrant detector 218 enables microcontroller 230 to accurately track light source 202 with simpler control-system hardware and software than is required for non-linear control signals.

In an embodiment, multi-axis mount 215 is controlled by a microcontroller 230, which receives control signal 210S. Incoherent-light iridectomy system 200 may also include a user interface 280 that is configured to stop propagation of light 202L to delivery optics unit 170 by controlling a shutter 221 of light collector 220. Delivery optics unit 170 outputs light 270L to a spot 229 centered at a location 194S on iris 194.

Optical fiber unit 250 includes one or more optical fibers. For example, optical fiber unit includes multiple optical fibers that collect light 202L at light collector 220. Light 220L propagating through these multiple fibers may be coupled into a single fiber received by slit-lamp adaptor 260. Similarly, incoherent-light iridectomy system 200 may include multiple light collectors 220 optically coupled to respective optical fiber units 250 that are coupled into a single fiber received by slit-lamp adaptor 260.

Light collector 220 includes a lens unit 222 therein for coupling light 202L into optical fiber unit 250. Optical fiber unit 250 has a first end 251 that is for example coplanar with a focal plane 222F of lens unit 222.

Figure 3:
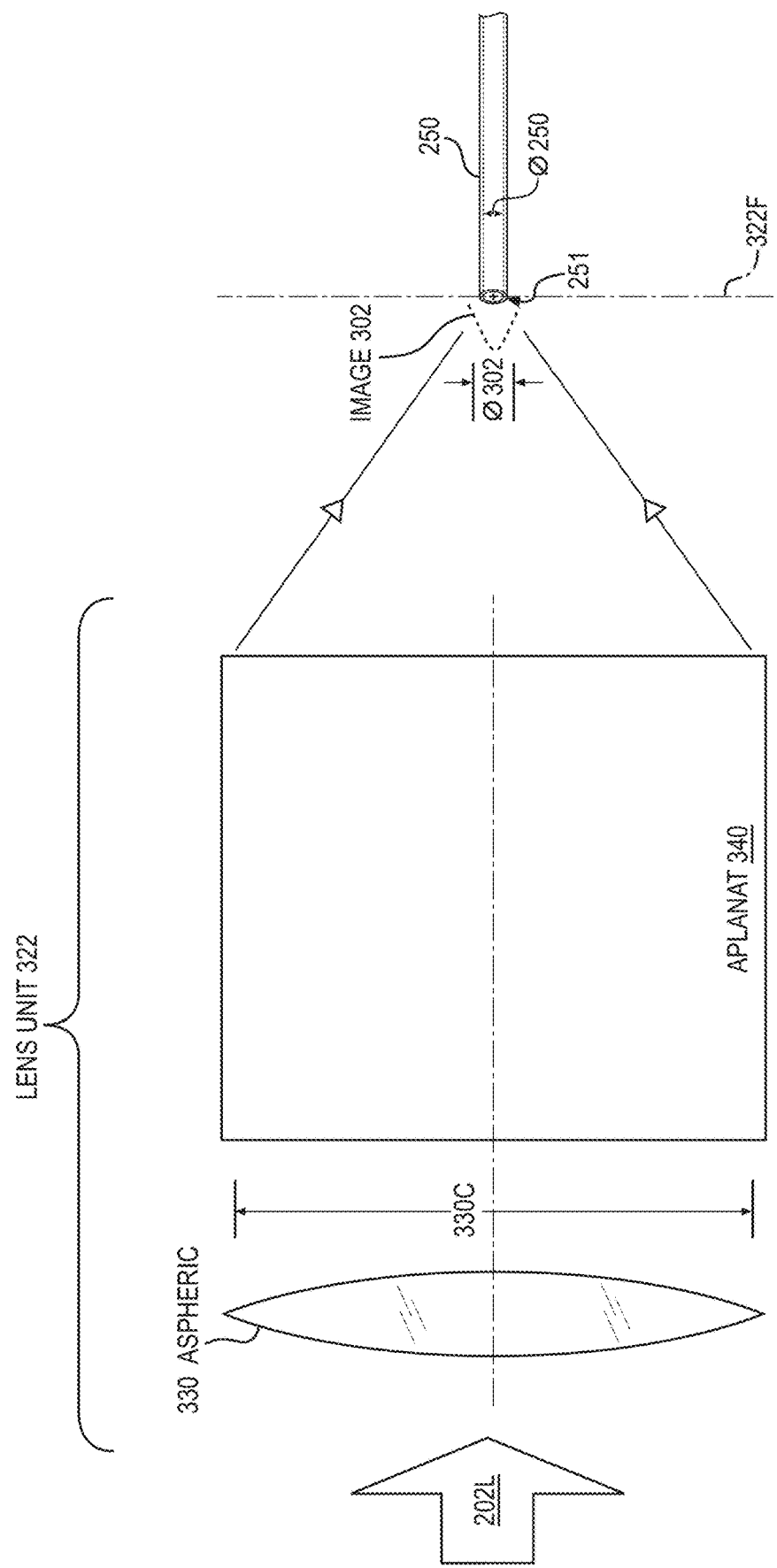
FIG. 3 shows the coupling of light into an optical fiber by the incoherent-light iridectomy system of FIG. 2, in an embodiment.

FIG. 3 is a cross-sectional view of a lens unit 322, which as an example of lens unit 222. Lens unit 322 includes an aspheric lens 330 and an aplanat 340 that is coaxial thereto. Lens unit 322 has a relative aperture (f-number) $N_{322}$ that satisfies $N_{322} < 1.2$. For example, $N_{322} = 1.0$. Lens unit 322 may also include a spectral filter, such as a band-pass filter that blocks ultra-violet components of light 202L while transmitting at least a part of the visible components of light 202L. Lens unit 322 has a numerical aperture $NA_{322}$ that satisfies $0.50 < NA_{322} < 0.60$. For example, $NA_{322} = 0.55$. Aspheric lens 330 has a clear aperture 330C between one hundred and one hundred twenty millimeters. Numerical aperture $NA_{322}$ and clear aperture 330C enable lens unit 322 to capture a sufficient amount of light 202L such that light 220L has sufficient power to form a hole in iris 194.

FIG. 3 shows lens unit 322 focusing light 202L to an image 302 at an image plane 322F, which is coplanar with first end 251 of optical fiber unit 250. Image 302 has a diameter $\emptyset_{302}$ that is for example 800 µm. Image 302 has for example a Gaussian intensity distribution with a beam waist equal to one-half of diameter $\emptyset_{302}$. First end 251 has a numerical aperture $NA_{250}$ that satisfies $0.40 < NA_{250} < 0.60$. First end 251 has a core diameter $\emptyset_{250}$ that satisfies $500 \ \mu m < \emptyset_{250} < 700 \ \mu m$. For example, $NA_{250} = 0.48$ and $\emptyset_{250} = 600$.

In an exemplary mode of operation, light 202L that reaches light collector 220 is sunlight with irradiance $E_e = 1035$ W/m². Approximately forty-two percent of Ee is visible light such that the visible irradiance $E_{vis} = 435$ W/m². When clear aperture 330C equals 0.114 meters, light collector 220 has total collection area $A_{220} = 0.0102$ m² (102 cm²) and hence captures $E_{vis} = 4.44$ Watts. The amount of $E_{vis}$ that coupled into optical fiber unit 250 from light collector is denoted herein as Ec and may be estimated using numerical apertures $NA_{250}$, $NA_{322}$ and diameters $\emptyset_{250}$, $\emptyset_{302}$ according to $$E_c \cong \left(\frac{NA_{250}}{NA_{322}}\right)^2 \left(\frac{\emptyset_{250}}{\emptyset_{302}}\right)^2$$

$E_{vis}$. When $NA_{250}$=0.48, $NA_{322}$=0.55, $\varnothing_{250}$=600 µm, and $\varnothing_{302}$=1.05 mm, the optical power in optical fiber unit 250 is $E_e$=1.1 Watts (i.e., greater than 1 Watt), which is sufficient for forming a hole in iris 194.

Figure 4:
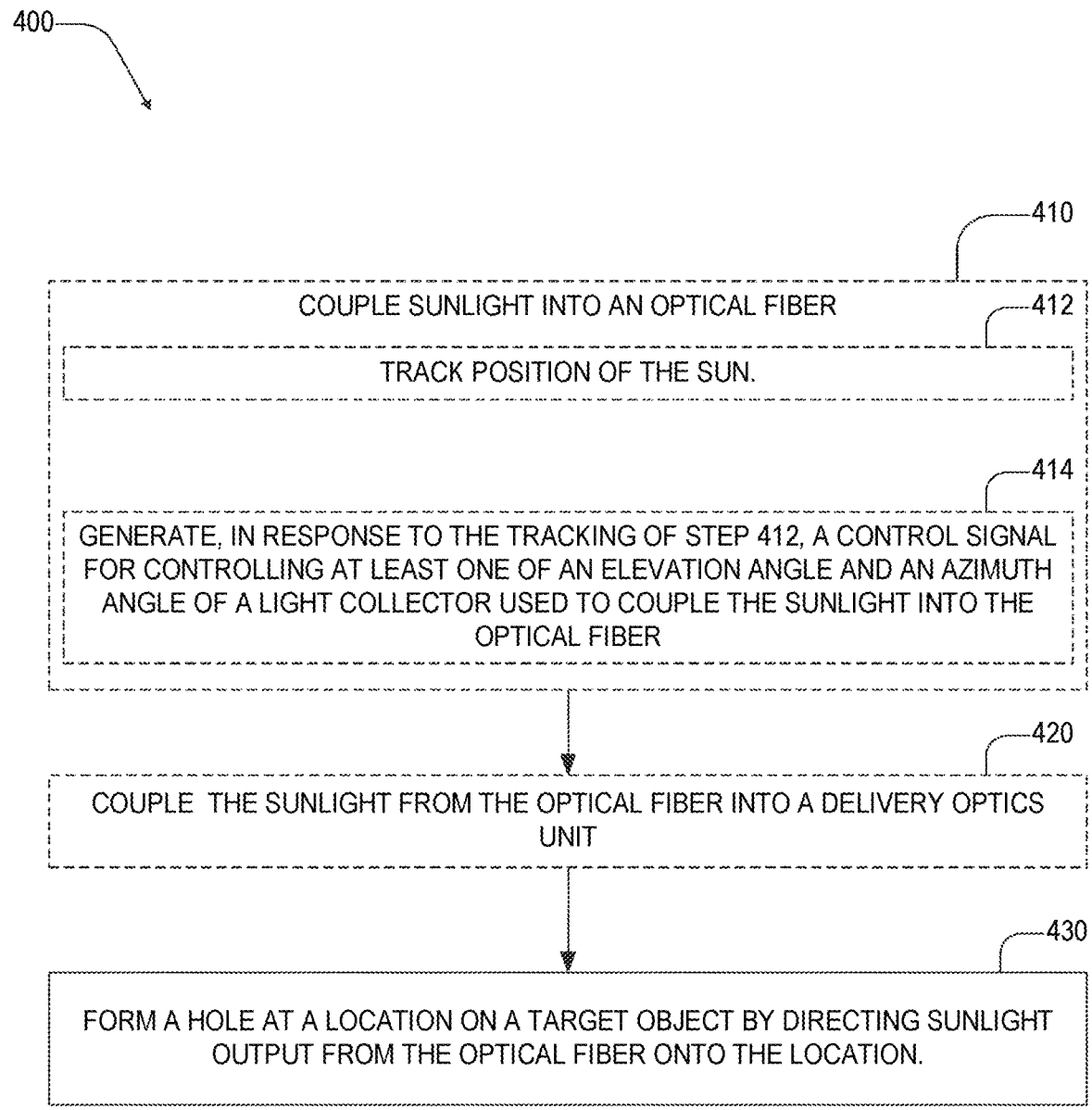
FIG. 4 is a flowchart illustrating an exemplary incoherent-light iridectomy method, in an embodiment.

FIG. 4 is a flowchart illustrating an exemplary iridectomy method 400. While method 400 is referred to herein as an "iridotomy method," method 400 may be employed in applications other than iridectomy, such as those listed above regarding system 200.

Method 400 includes step 430, and may also include steps 410 and 420. Step 410 includes coupling light into an optical fiber. In an example of step 410, light collector 220 couples light 202L into optical fiber unit 250, which carries output light 220L. Step 410 may include step 412, which is one of tracking the position of the sun. In an example of step 412, solar tracker 210 tracks the position of light source 202. Step 410 may also include step 414 of generating, in response to the tracking of step 412, a control signal for controlling at least one of an elevation angle and an azimuth angle of a light collector used to couple the light into the optical fiber. In an example of step 414, solar tracker 210 generates control signal 210S that is received by microcontroller 230, which controls at least one of an elevation angle and an azimuth angle of light collector 220.

Step 420 includes coupling the light from the optical fiber into a delivery optics unit. In an example of step 420, slit-lamp adaptor 260 couples output light 220L into delivery optics unit 170.

Step 430 includes forming a hole at a location on a target object by directing light output from an optical fiber onto the location. The target object can be tissue, including soft tissue such as tissue of an eye. In an example of step 430, light 270L output from delivery optics unit 170 forms a hole at location 194S, FIG. 2. Without departing from the scope hereof, the target object may be an object other than an eye or a region thereof. Examples of such target locations (location 194S) include those associated with above-mentioned dermatological procedures and other applications of system 200.

Figure 5:
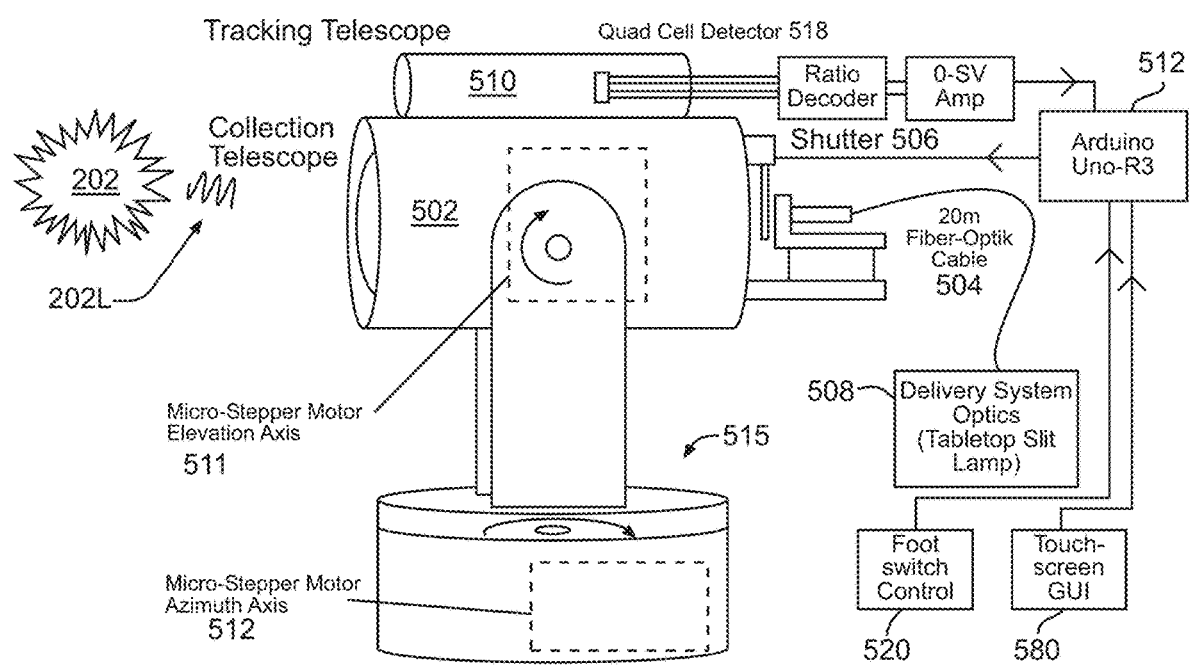
FIG. 5 is a block diagram of an incoherent-light iridectomy system, which is an example of the incoherent-light iridectomy system of FIG. 2.

FIG. 5 depicts a block diagram of an incoherent-light iridectomy system 500, which is an example of incoherent-light iridectomy system 200. A collection telescope 502 collects light 202L and focuses it onto a 600-micron diameter optical fiber 504 when the shutter is in the open position. Optical fiber 504 is an example of optical fiber unit 250. Light 202L travels in optical fiber 504 and exits into a traditional ophthalmic delivery system 508 (such as, but not limited to a table-top slit lamp), which is an example of delivery optics unit 170. By controlling the duration of the exposure using shutter 506, the ophthalmologist can create the required hole in the patient's iris.

Embodiments herein operate to keep the image of light source 202 precisely on the input end (e.g., first end 251) of the fiber optic (e.g., optical fiber 504). This requires precise tracking of light source 202 for a period of time over the procedure that can extend upwards of fifteen minutes. Collection telescope 502 features a 125 mm diameter aspheric lens, which is an example of lens unit 222. An aplanatic lens is also used to speed up the beam, reduce the size of light source 202's image, and match the numerical aperture of optical fiber 504. In this example, light source 202 is imaged to a spot having an 800-micron diameter and the power collected in the visible spectrum at the input end of optical fiber 504 is 1.9 watts. Most laser based iridectomy systems operate at 1 watt or less. This means that the alternative system disclosed here is powerful enough to perform the procedure.

Mount 515 is an example of mount 215, and has an Alt-El (altazimuth-elevation) design. Each axis (e.g. elevation axis and azimuth axis) has an intelligent micro stepper motor 511, 512, controlled by a controller 514 (shown, but not limited to, a single Arduino R3 Uno computer). One revolution of either axis represents 102,400 micro-steps, for example.

In embodiments, such as that shown in FIG. 5, a tracking telescope 510 may be mounted to the collection telescope 502 and precisely aligned, such as using boresight alignment. Position information from the tracking telescope 510 is sent to the computer 514, which generates correction signals (X and Y) that are then sent to the respective stepper motors 511, 512. Because of the linearity of the tracker design, only one iteration is necessary to bring the optics within collector telescope 502 into perfect alignment. This provides the advantage that the system 500 may meet the timing requirements to accurately and adequately perform the procedure.

Figure 6:
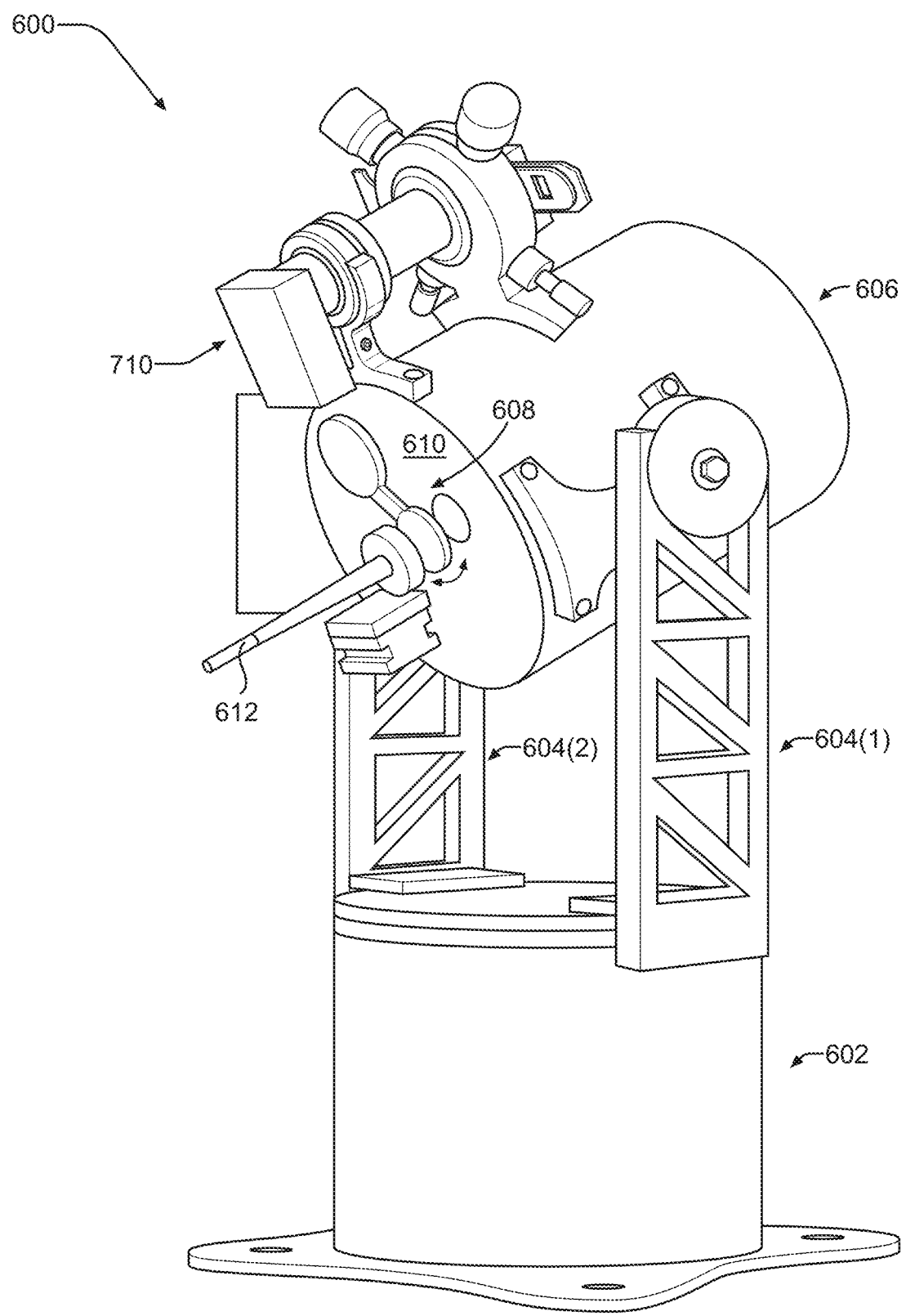
FIG. 6 is a CAD drawing of an incoherent-light iridectomy system, which is an example of the incoherent-light iridectomy system of FIG. 5.

FIG. 6 depicts a CAD drawing of incoherent-light iridectomy system 600, which is an example of incoherent-light iridectomy system 500. A base 602 of system 600 houses the azimuth stepper motor (e.g. motor 512), gearing, a large diameter circular crossed roller bearing, the computer (e.g. computer 514), and a power supply that may be coupled to one or more of the components discussed herein. A frame 604, which may include two forks 604(1), 604(2) hold collection telescope 606 (which is an example of the collection telescope 502). Either one (or both) of the forks 604 houses the elevation stepper motor and gearing (e.g. motor 511). A solenoid-actuated shutter 608 (which is an example of shutter 506), controlled using controller 514 for example, is mounted on a back plate 610 of collection telescope 602. The ophthalmologist sets the duration of the exposure of shutter 608 on the software's GUI (Graphical User Interface) 580. The GUI 580 may include hardware, such as an input device and display, that allows the ophthalmologist to interact with computer 514 to control the system 500, 600. When the ophthalmologist is satisfied with the alignment of system 600 with the patient's iris, the ophthalmologist hits the footswitch (e.g. footswitch 520 shown in FIG. 5). That motion causes the computer-controlled solenoid to open and close a shutter 608 for the precise interval selected by the ophthalmologist. Telescope back plate 610 may also include an adjustable mount that holds the fiber optic cable. The fiber optic cable can be adjusted so that the focus of light source 202's image will enter at the appropriate distance to enable coupling the maximum amount of energy into the fiber optic cable 612, which is an example of optical fiber 504.

Figure 7:
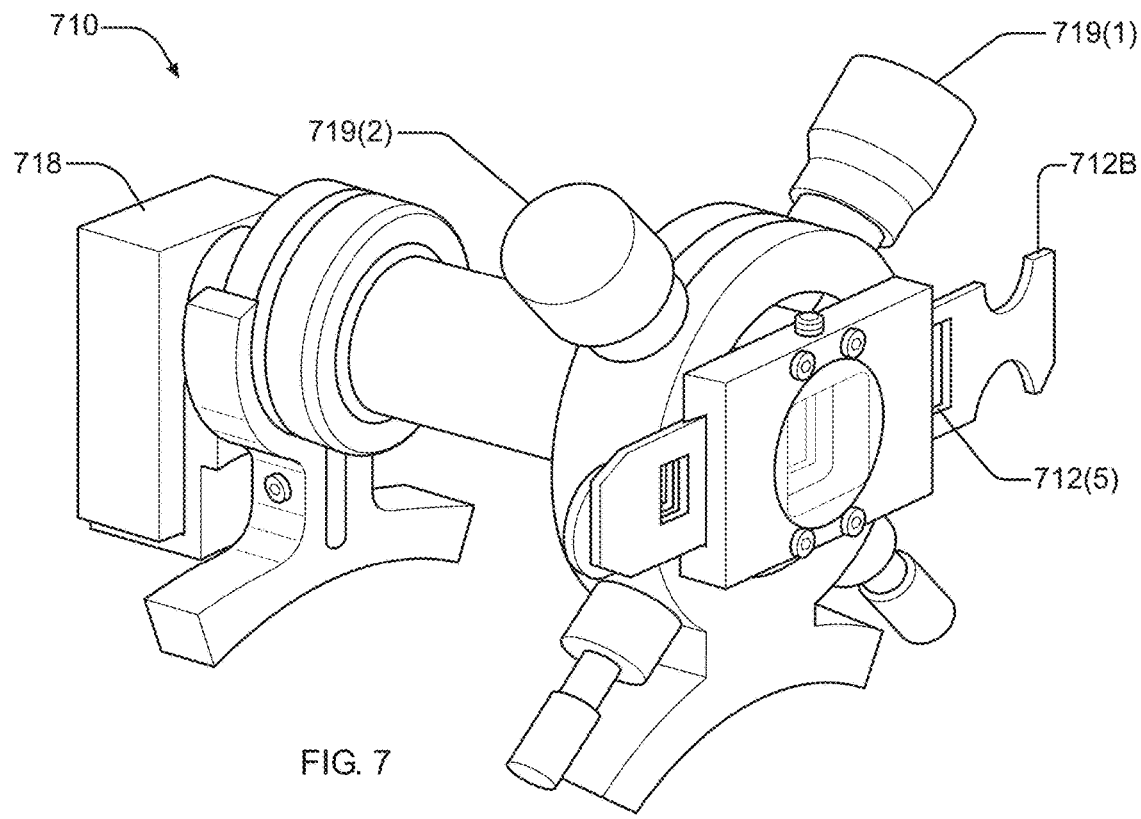
FIG. 7 is an isometric view of a tracking telescope of the incoherent-light iridectomy system of FIG. 6, in an embodiment.

Mounted on top of the collection optics is a tracking telescope 710, shown in more detail in FIG. 7. Tracking telescope 710 is an example of solar tracker 210, FIG. 2, and tracking telescope 510, FIG. 5. Tracking telescope 710 collects light 202L using a quadrant detector 718 placed sufficiently inside of focus where the Fresnel diffraction optics is minimum so that the 'square-ness' of the square aperture (one of apertures 712(1-5)) placed in front of an objective lens 714 is preserved. Apertures 712, objective lens 714, and detector 718 are examples of aperture 212, lens 214, and detector 518, respectively.

It is a true imaging system that recognizes that the square shape of the aperture is maintained inside of focus as a result of Fresnel diffraction. This simple system includes a square aperture, an objective lens and a quadrant detector placed inside of focus.

There is a range 718R in which quadrant detector 718 may be positioned along the optical axis where the image formed by lens 714 is sufficiently square while being small enough to enable precise detection of movement. The beam transmitted by lens 714 is square in a plane immediately after the lens, but the beam is too large for quadrant detector 718 to detect motion. The beam is sufficiently small at the focal point and further from the lens, which improves tracking sensitivity. However, at the focal point the beam no longer square, the response of the quadrant detector is nonlinear, which delays accurate motion detection and degrades tracking quality, as discussed below. An optimal position for quadrant detector 718 along the optical axis optimized a tradeoff between "squareness" and sensitivity, since the greater distance from the spot, the longer the optical lever, and therefore the greater the sensitivity.

For example, lens 714 may be an achromatic doublet lens having a focal length f=100-mm. When the aperture 712 was a square with side length s=2.5 mm, an optimal position corresponded to 75±5 mm from lens 714 at a wavelength $\lambda_0$=546 nm. A square aperture with side length s may be viewed as equivalent to a circular aperture having a radius a that is the average of radii of an inscribed circle and circumscribed circle: $a=3s/(4\sqrt{2})\cong 0.53s$. These parameters correspond to distance parameter $N_D=a^2/\lambda_0 d$ between 40 and 46. Distance parameter $N_D$ equivalent to the Fresnel number. In an embodiment of solar iridectomy system 200, quadrant detector is located a distance $d_{218}$ from lens 214, along the optical axis of lens 214, such that $d_{218}$ satisfies distance parameter $N_D$ between 40 and 46 at a wavelength included in light 202L, for example, a visible light wavelength.

Figure 8:
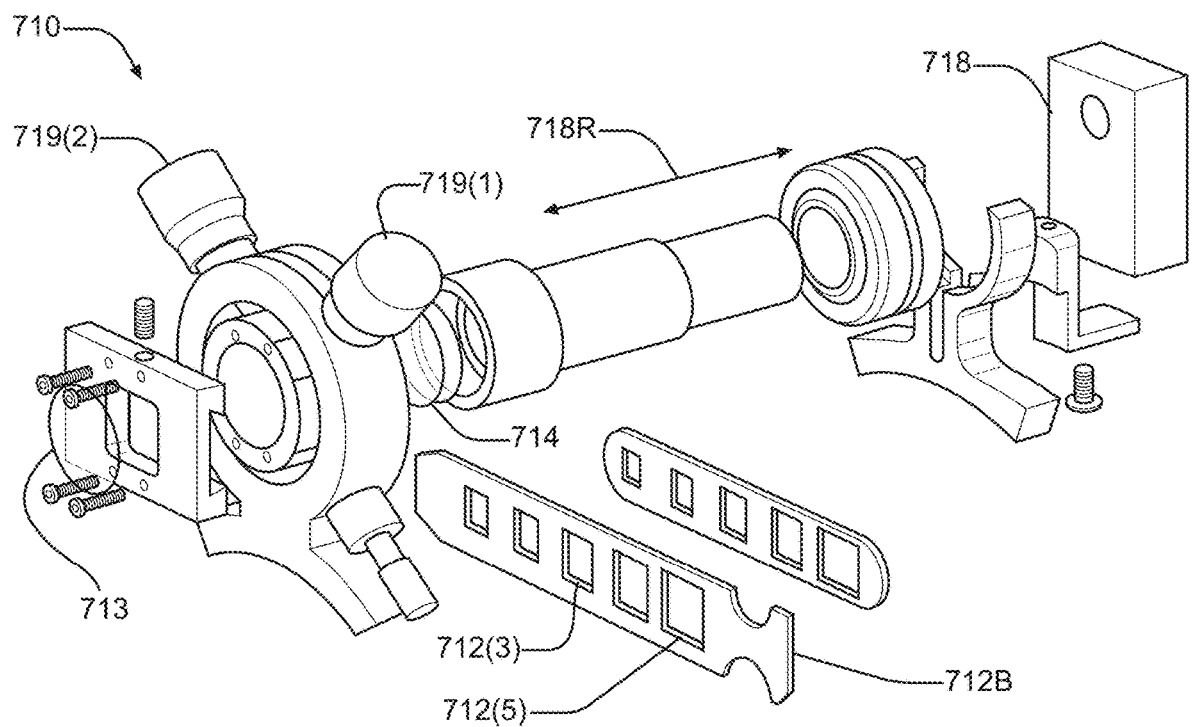
FIG. 8 is an exploded view of the tracking telescope of FIG. 7.

FIG. 8 shows an exploded view of tracking telescope 710. Tracking telescope 710 is configured to mount directly to the collection telescope, e.g., light collector 220. Tracking telescope 710 may include two 80-pitch micrometers 719(1,2) mounted at a right angle with a spherical bearing so that tracking telescope 710 can be bore-sighted precisely. Progressively sized square apertures 712(1-5) mounted on a sliding bar 712B with detents. The sliding bar may include more or fewer than five square apertures 712 without departing from the scope hereof. The sliding bar enables selection of an aperture that gives us the best results. In order not to saturate quadrant detector 718, tracking telescope 710 may include an optical filter 713. Optical filter 713 may be a neutral density filter having an optical density between five and eight.

The unique configuration/design/arrangement of the Eidolon tracking system makes it higher performance than other closed-loop precision tracking systems.

Modern closed-loop precision tracking systems (CLPTS) involve electronics and a quad cell. The quad cell is used to determine the position of the tracked object by detecting a signal emitted by that object. Using the information provided by the quad cell, the electronics readjust the position of the system where the quad cell is mounted.

In CLPTS, the signal received by the quad cell typically has a round shape and the quad cell has a square or rectangular active area. As a result, prior art CLPTS have non-linear response because the convolution of a rectangle and a circle (see FIG. 9). Because of the circular shape of the beam, the shape of the region generating a voltage on the quad cell is circular, and it takes the tracking system's electronics multiple iterations to align the center of the circle with the center of the quad cell (see FIG. 10A).

As illustrated by FIG. 10A, the beam and the quad cell are misaligned. Each quadrant will produce a signal proportional to the amount of incident light energy. The ratio of the signals will predict the degree of misalignment. FIG. 10B, by contrast, represents perfect alignment of the beam with the quadrant detector. Each quadrant will produce equal signal.

Therefore, optimal CLPTS align the quad cell and the beam with the least iterations. This is best achieved when the relationship between the position of the beam and of the quadrant detector is linear. This relationship can be studied through the convolution of the shape of the quad cell and of the beam.

Figure 11:
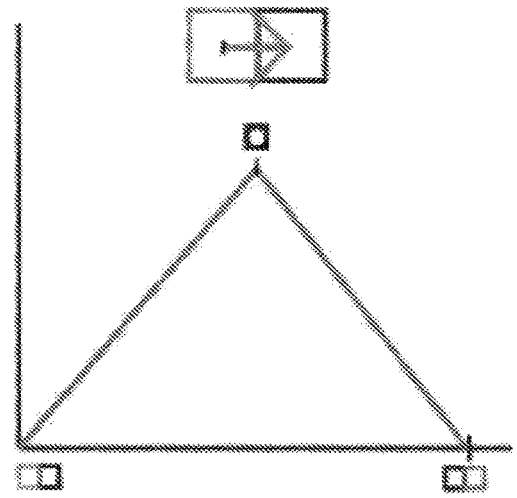
FIG. 11 is a graphical depiction of the convolution of two rectangular pulses.

FIG. 11 illustrates that the convolution of two rectangular pulses yields a triangle. Thus, for the position of the center of the quad cell and the position of the center of the signal to have a linear relationship, both should be represented by functions that are rectangular pulses.

The following demonstrates that, for a linear response of a CLPTS, the shape of a quad cell and the shape of an optical beam incident on the quad cell should be rectangular. Let f $\in$R and g$\in$R be functions that gives the shape of the quad cell and the beam shape incident on the quad cell respectively: When f is a square with side length a, e.g., f(x,y)={1, x$\in$[0, a) and y$\in$[0, a, 0, otherwise}. When the beam is circular, $g(r)^2=1-r^2$, $(r^2=(x^2+y^2))$, the convolution of f and g yields a Gaussian curve (see FIG. 9).

When the beam looks like a square, side length a' after going through the square aperture, e.g., g(x,y)={1, x$\in$[0, a') and y$\in$[0, a', 0, otherwise}, the convolution of f and g yields a triangular curve, as shown in FIG. 11. Therefore, in order for the convolution of f and g to be linear, both f and g need to be rectangular. More precisely, in this context both f and g would need to be square.

Figure 12:
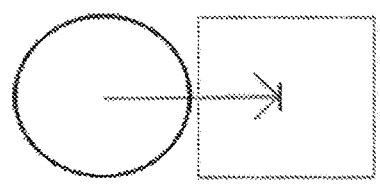
FIG. 12 is a graphical depiction of the convolution of a circle with a square at five points.
Figure 12:
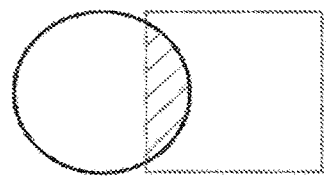
Figure 12:
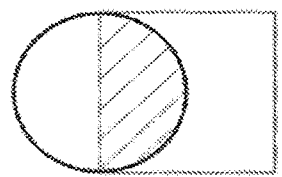
Figure 12:
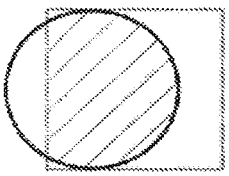
Figure 12:
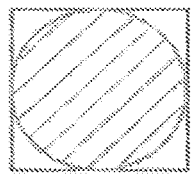
Figure 13:
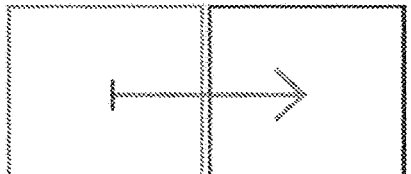
FIG. 13 is a graphical depiction of the convolution of two squares at five points.
Figure 13:
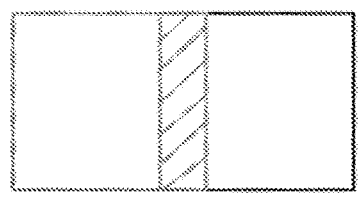
Figure 13:
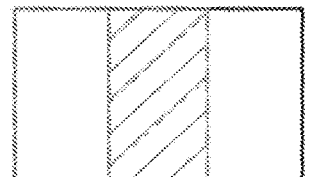
Figure 13:
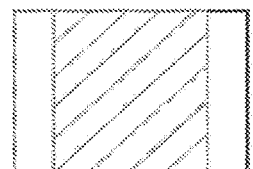
Figure 13:
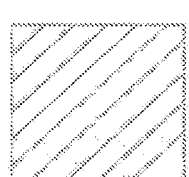

FIGS. 12 and 13 illustrate a graphical approach to understanding the aforementioned convolutions. FIG. 12 shows the convolution of a circle with a square at five given points. FIG. 13 shows the convolution of two squares at five given points.

Figure 14:
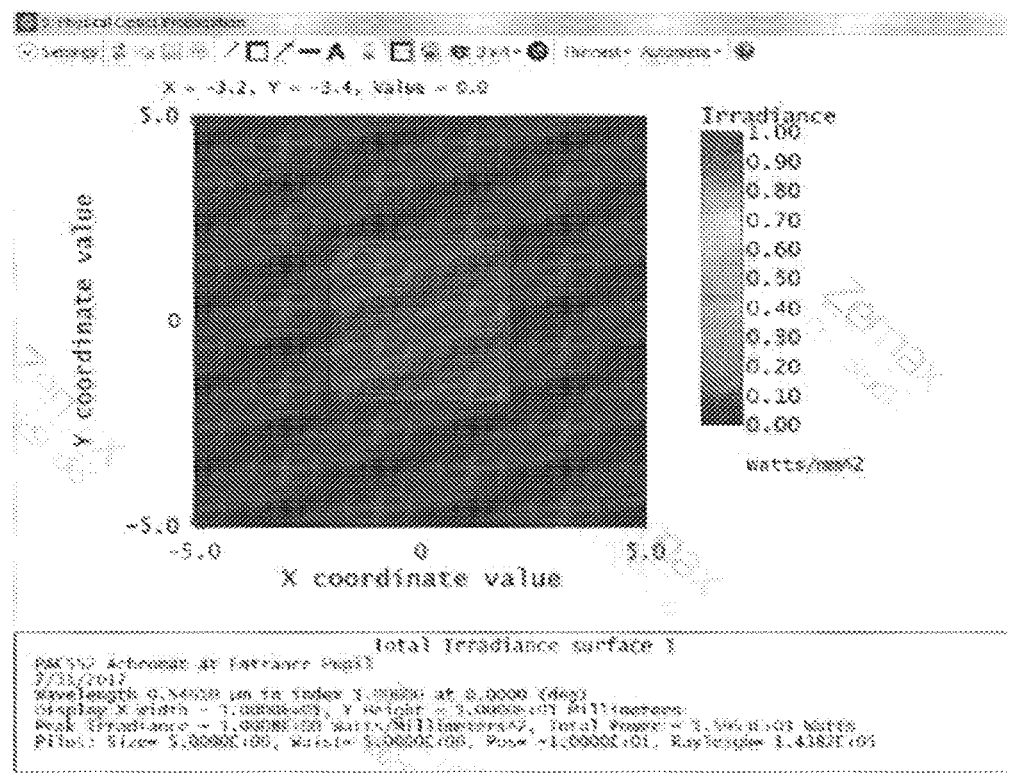
FIG. 14 illustrates physical optics propagation (POP) of a uniformly illuminated square aperture at an entrance pupil.
Figure 15:
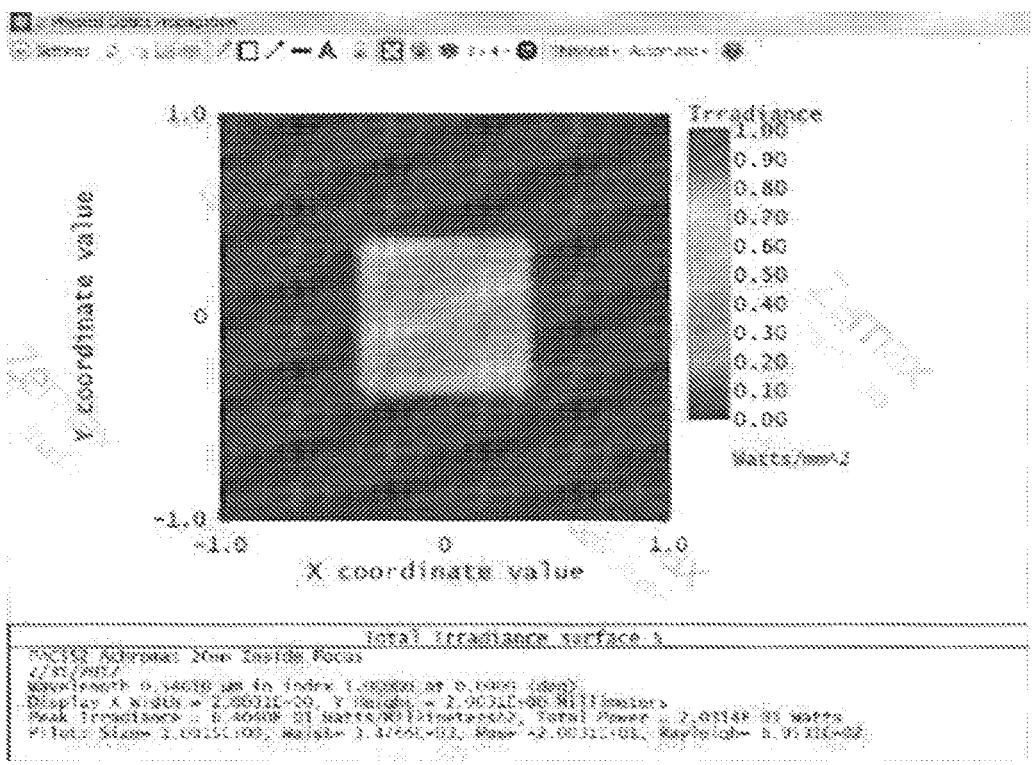
FIG. 15 illustrates preservation of a square beam shape of illumination transmitted by the square aperture of FIG. 14.
Figure 16:
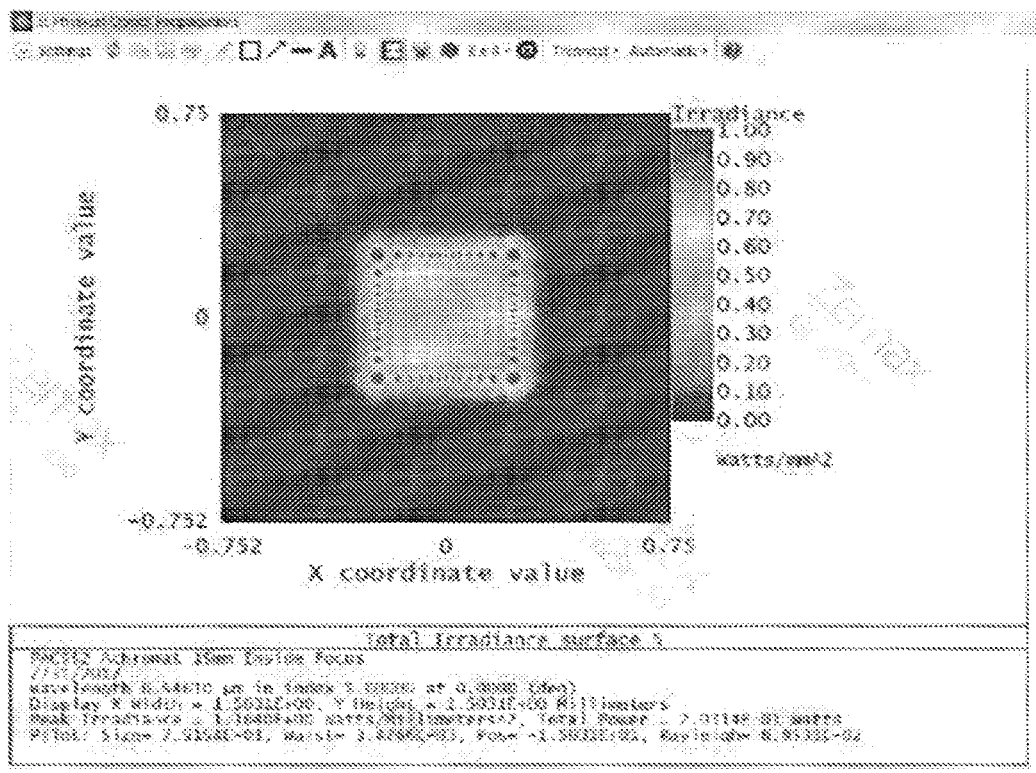
FIG. 16 illustrates preservation of a square beam shape with somewhat uniform illumination of the square aperture of FIG. 14.

FIGS. 14-16 show results of a Zemax® physical optics propagation simulation of illumination through a square aperture, such a square aperture 212 of solar tracker 210. The beam is focused by lens 214 of solar tracker 210. The simulation enables determination of the effects of Fresnel diffraction and prediction of how close to the image plane inside focus the beam still resembles the square aperture.

Figure 17:
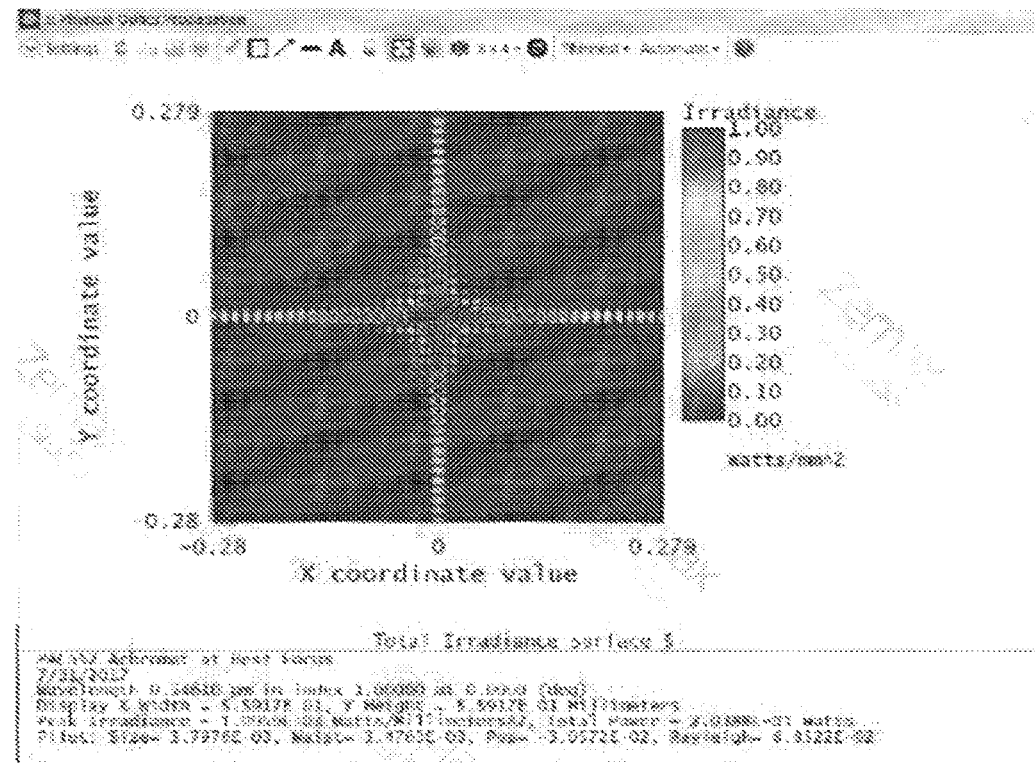
FIG. 17 illustrates POP of a highly non-uniform beam with no square shape at image plane.

FIG. 14 shows the highly uniform square spot at the entrance pupil as predicted by a Zemax® physical optics propagation simulation. The results are coherent with what one would expect. FIG. 15 shows the beam twenty millimeters inside of focus (the objective, e.g., lens 214, has an EFL=100 mm in this example). FIG. 15 illustrates that the square spot shape has been preserved and that the uniformity of illumination is good. FIG. 16 shows the beam fifteen millimeters inside of focus. The beam remains square but the uniformity of illumination is somewhat degraded. FIG. 17 shows the beam at best focus where all the square shape is gone and the uniformity of illumination is completely destroyed.

Features described above as well as those claimed below may be combined in various ways without departing from the scope hereof. The following examples illustrate some possible, non-limiting combinations:

(A1) An incoherent-light iridectomy system includes a light collector, delivery optics, and an optical fiber unit. The light collector is configured to capture light. The delivery optics unit is configured to deliver the captured light to an eye of a glaucoma patient. The optical fiber unit optically connects an output of the light collector to the delivery optics unit.

(A2) In the incoherent-light iridectomy system denoted by (A1), the delivery optics unit may include a corneal microscope.

(A3) In an incoherent-light iridectomy system denoted by one of (A1) and (A2), the delivery optics unit may include a slit lamp.

(A4) An incoherent-light iridectomy system denoted by one of (A1) through (A3), in which the light is sunlight, may further include a solar tracker and multi-axis mount. The solar tracker is configured to output a control signal. The multi-axis mount is communicatively coupled to the solar tracker and is configured to changing, in response to the control signal, at least one of an elevation angle and azimuthal angle of the light collector.

(A5) In the incoherent-light iridectomy system denoted by (A4), the solar tracker may include a lens between a rectangular aperture and a quadrant detector (A6) In an incoherent-light iridectomy system denoted by one of (A1) through (A5), the light collector may have a collection area exceeding one hundred square centimeters.

(A7) An incoherent-light iridectomy system denoted by one of (A1) through (A6), may further include an incoherent light source, optically coupled to the light collector, for producing the light.

(B1) An incoherent-light iridectomy method includes forming a hole at a location on an eye by directing light output from an optical fiber onto the location.

(B2) In the incoherent-light iridectomy method denoted by (B1), the light may be sunlight.

(B3) The incoherent-light iridectomy method denoted by one of (B1) and (B2) may further include coupling the light into the optical fiber.

(B4) An incoherent-light iridectomy method denoted by one of (B1) through (B3), may further include, prior to the step of forming a hole, coupling the light from the optical fiber into a delivery optics unit.

(B5) In an incoherent-light iridectomy method denoted by (B4), the delivery optics unit may include a corneal microscope.

(B6) In an incoherent-light iridectomy system denoted by one of (B4) and (B4), the delivery optics unit may include a slit lamp.

(B7) In an incoherent-light iridectomy method denoted by one of (B1) through (B6), the hole may have a diameter less than six-hundred micrometers.

(B8) In an incoherent-light iridectomy method denoted by one of (B1) through (B6), the hole may have a diameter less than seventy micrometers.

Changes may be made in the above iridectomy methods and iridectomy systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present iridectomy method and iridectomy system, which, as a matter of language, might be said to fall therebetween.

What is claimed is:

1. A light delivery system comprising:
    a solar tracker including a rectangular aperture that delivers light to a quadrant detector, wherein the solar tracker is configured to output a control signal;
    a light collector configured to capture light from an incoherent light source, wherein the captured light is sunlight;
    a delivery optics unit for delivering the captured light to a target object;
    an optical fiber unit optically connecting an output of the light collector to the delivery optics unit; and
    a multi-axis mount communicatively coupled to the solar tracker and configured to change, in response to the control signal, at least one of an elevation angle and azimuthal angle of the light collector.

2. The light delivery system of claim 1, wherein the delivery optics unit includes a corneal microscope or an ophthalmoscope.

3. The light delivery system of claim 1, wherein the delivery optics unit includes a slit lamp.

4. The light delivery system of claim 1, wherein the delivery optics unit includes a zoom lens.

5. The light delivery system of claim 1, wherein the solar tracker includes a lens between the rectangular aperture and the quadrant detector.

6. The light delivery system of claim 5, wherein the lens forms a rectangular image on the quadrant detector in response to receiving light from the rectangular aperture.

7. The light delivery system of claim 6, wherein the rectangular aperture corresponds to one of a plurality of progressively sized square apertures defined by a sliding bar.

8. The light delivery system of claim 1, wherein the light collector includes an aspheric lens and an aplanat configured to focus the captured light to an image at an image plane that is coplanar with an end of the optical fiber unit.

9. The light delivery system of claim 1, wherein the light collector defines a collection area exceeding one hundred square centimeters.

10. A method of performing a surgical procedure comprising:
    determining a position of an incoherent light source, including delivering light from the incoherent light source through a square or rectangular aperture to form a rectangular image on a quadrant detector;
    capturing light from the incoherent light source in response to determining the position;
    communicating the captured light to an optical fiber; and
    forming an hole at a location on a target object by directing the captured light from the optical fiber onto the location.

11. The method of claim 10, wherein the light is sunlight.

12. The method of claim 11, further comprising, prior to the step of forming the hole, communicating the captured light from the optical fiber to a delivery optics unit.

13. The method of claim 12, wherein the delivery optics unit includes a corneal microscope.

14. The method of claim 12, wherein the delivery optics unit includes a slit lamp.

15. The method of claim 10, wherein an optical power of the captured light communicated to the optical fiber is greater than 1 Watt.

16. The method of claim 10, wherein the forming step results in the hole having a diameter of less than six-hundred micrometers.

17. The method of claim 10, wherein the forming step results in the hole having a diameter of less than seventy micrometers.

18. The method of claim 10, wherein the target object is soft tissue.

19. The method of claim 18, wherein the soft tissue is tissue of an eye.

* * * * *